United States Patent
Wu et al.

(10) Patent No.: US 12,202,896 B2
(45) Date of Patent: Jan. 21, 2025

(54) CAR-T CELLS WITH HUMANIZED CD19 SCFV WITH MUTATION IN CDR 1 REGION

(71) Applicant: ZHEJIANG RUIJIAMEI BIOTECH CO., LTD., Shaoxing (CN)

(72) Inventors: Lijun Wu, Richmond, CA (US); Vita Golubovskaya, Richmond, CA (US)

(73) Assignee: ZHEJIANG RUIJIAMEI BIOTECH CO., LTD., Shaoxing (CN)

( * ) Notice: Subject to any disclaimer, the term of this patent is extended or adjusted under 35 U.S.C. 154(b) by 820 days.

(21) Appl. No.: 17/334,417

(22) Filed: May 28, 2021

(65) Prior Publication Data

US 2021/0395362 A1 Dec. 23, 2021

Related U.S. Application Data

(63) Continuation of application No. PCT/CN2019/109633, filed on Sep. 30, 2019.

(60) Provisional application No. 62/773,112, filed on Nov. 29, 2018.

(51) Int. Cl.
| | |
|---|---|
| *C07K 16/28* | (2006.01) |
| *A61K 39/00* | (2006.01) |
| *A61P 35/00* | (2006.01) |
| *C12N 5/0783* | (2010.01) |
| *C07K 5/04* | (2006.01) |

(52) U.S. Cl.
CPC ...... *C07K 16/2803* (2013.01); *A61K 39/4611* (2023.05); *A61K 39/4631* (2023.05); *A61K 39/464412* (2023.05); *A61P 35/00* (2018.01); *C12N 5/0636* (2013.01); *A61K 2239/48* (2023.05); *C07K 2317/622* (2013.01)

(58) Field of Classification Search
CPC ............ C07K 14/7051; C07K 2317/24; C07K 2317/622; C07K 2319/03; C12N 15/63; C12N 5/0636; A61P 35/00; A61K 2239/48; A61K 39/4611; A61K 39/4631; A61K 39/464412
See application file for complete search history.

(56) References Cited

U.S. PATENT DOCUMENTS

| | | | |
|---|---|---|---|
| 11,034,763 B2 * | 6/2021 | Wu | A61P 35/00 |
| 11,725,053 B2 * | 8/2023 | Wu | C07K 14/7051 |
| | | | 530/388.73 |
| 2018/0153977 A1 | 6/2018 | Wu et al. | |

FOREIGN PATENT DOCUMENTS

| | | |
|---|---|---|
| CN | 107226867 A | 10/2017 |
| CN | 107312091 A | 11/2017 |
| CN | 107793478 A | 3/2018 |
| WO | 2017/172952 A1 | 10/2017 |

OTHER PUBLICATIONS

International Search Report and Written Opinion for Application No. PCT/CN2019/109633, mailed Dec. 27, 2019.
International Preliminary Report on Patentability for Application No. PCT/CN2019/109633, mailed Jun. 10, 2021.
GENBANK Submission; NCBI, Accession No. ADM64594.1; FMC63-28Z receptor protein [synthetic construct]. Kochenderfer et al.; Jun. 11, 2012.
Kochenderfer et al., Construction and preclinical evaluation of an anti-CD19 chimeric antigen receptor. J Immunother. Sep. 2009;32(7):689-702. doi: 10.1097/CJI.0b013e3181ac6138.
Qian et al., The novel anti-CD19 chimeric antigen receptors with humanized scFv (single-chain variable fragment) trigger leukemia cell killing. Cell Immunol. Jun.-Jul. 2016;304-305:49-54. doi: 10.1016/j.cellimm.2016.03.003. Epub Mar. 14, 2016.
Zhang et al., Construction and in vitro verification of a new humanized anti-CD19 CAR-T cells with high affinity. Zhonghua Xue Ye Xue Za Zhi. Jun. 14, 2018;39(6):465-470. doi: 10.3760/cma.j.issn.0253-2727.2018.06.005.
PCT/CN2019/109633, Dec. 27, 2019, International Search Report and Written Opinion.
PCT/CN2019/109633, Jun. 10, 2021, International Preliminary Report on Patentability.
EP 19888842.2, Nov. 22, 2022, Extended European Search Report.
Extended European Search Report for Application No. 19888842.2, mailed Nov. 22, 2022.

* cited by examiner

*Primary Examiner* — Bao Q Li
(74) *Attorney, Agent, or Firm* — Wolf, Greenfield & Sacks, P.C.

(57) ABSTRACT

Provided is a humanized CD19 single-chain variable fragment (scFv) having a mutation of valine to glycine in CDR1, comprising VH having the amino acid sequence of SEQ ID NO: 6 and VL having the amino acid sequence of SEQ ID NO: 5. Also provided is a CD19 chimeric antigen receptor fusion protein comprising from N-terminus to C-terminus: (i) a single-chain variable fragment (scFv), (ii) a transmembrane domain, (iii) at least one co-stimulatory domains, and (iv) an activating domain. This humanized CD19-CAR-T cells have specific killing activity with secretion of cytokine IFN-gamma in CAR-T cells in vitro and in vivo.

11 Claims, 6 Drawing Sheets
Specification includes a Sequence Listing.

SEQUENCE LISTING

<160> NUMBER OF SEQ ID NOS: 16

<210> SEQ ID NO 1
<211> LENGTH: 321
<212> TYPE: DNA
<213> ORGANISM: Artificial Sequence
<220> FEATURE:
<223> OTHER INFORMATION: CD19 VL

<400> SEQUENCE: 1

```
gatattcaga tgacccagag cccgagcagc ctgagcgcga gcgtgggcga tcgcgtgacc      60
attacctgcc gcgcgagcca ggatattagc aaatatctga actggtatca gcagaaaccg     120
ggcaaagcgc cgaaactgct gatttatcat accagccgcc tgcatagcgg cgtgccgagc     180
cgctttagcg gcagcggcag cggcaccgat tttaccctga ccattagcag cctgcagccg     240
gaagattttg cgacctatta ttgccagcag ggcaacaccc tgccgtatac ctttggcggc     300
ggcaccaaag tggaaattaa a                                               321

<210> SEQ ID NO 2
<211> LENGTH: 360
<212> TYPE: DNA
<213> ORGANISM: Artificial Sequence
<220> FEATURE:
<223> OTHER INFORMATION: CD19 VH

<400> SEQUENCE: 2
caggtgcagc tgcaggaaag cggcccgggc ctggtgaaac cgagcgaaac cctgagcctg      60
acctgcaccg tgagcggcgg cagcctgccg gattatggcg tgagctggat tcgccagccg     120
ccgggcaaag gcctggaatg gattggcgtg atttggggca gcgaaaccac ctattataac     180
agcgcgctga aaagccgcgt gaccattagc gtggatacca gcaaaaacca gtttagcctg     240
aaactgagca gcgtgaccgc cggcgatacc gcggtgtatt attgcgcgaa acattattat     300
tatggcggca gctatgcgat ggattattgg ggccagggca ccctggtgac cgtgagcagc     360

<210> SEQ ID NO 3
<211> LENGTH: 54
<212> TYPE: DNA
<213> ORGANISM: Artificial Sequence
<220> FEATURE:
<223> OTHER INFORMATION: linker

<400> SEQUENCE: 3
ggctccacct ctggatccgg caagcccgga tctggcgagg atccaccaa gggc              54

<210> SEQ ID NO 4
<211> LENGTH: 245
<212> TYPE: PRT
<213> ORGANISM: Artificial Sequence
<220> FEATURE:
<223> OTHER INFORMATION: CD19 scFv

<400> SEQUENCE: 4

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
```

```
                    115                 120                 125
Leu Gln Glu Ser Gly Pro Gly Leu Val Lys Pro Ser Glu Thr Leu Ser
        130                 135                 140

Leu Thr Cys Thr Val Ser Gly Gly Ser Leu Pro Asp Tyr Gly Val Ser
145                 150                 155                 160

Trp Ile Arg Gln Pro Pro Gly Lys Gly Leu Glu Trp Ile Gly Val Ile
                165                 170                 175

Trp Gly Ser Glu Thr Thr Tyr Tyr Asn Ser Ala Leu Lys Ser Arg Val
            180                 185                 190

Thr Ile Ser Val Asp Thr Ser Lys Asn Gln Phe Ser Leu Lys Leu Ser
        195                 200                 205

Ser Val Thr Ala Ala Asp Thr Ala Val Tyr Tyr Cys Ala Lys His Tyr
    210                 215                 220

Tyr Tyr Gly Gly Ser Tyr Ala Met Asp Tyr Trp Gly Gln Gly Thr Leu
225                 230                 235                 240

Val Thr Val Ser Ser
                245
```

<210> SEQ ID NO 5
<211> LENGTH: 107
<212> TYPE: PRT
<213> ORGANISM: Artificial Sequence
<220> FEATURE:
<223> OTHER INFORMATION: CD19 VL

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Gly Gly Thr Lys Val Glu Ile Lys
            100                 105
```

<210> SEQ ID NO 6
<211> LENGTH: 120
<212> TYPE: PRT
<213> ORGANISM: Artificial Sequence
<220> FEATURE:
<223> OTHER INFORMATION: CD19 VH

<400> SEQUENCE: 6

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ala Leu Lys
    50                  55                  60
```

```
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 7
<211> LENGTH: 18
<212> TYPE: PRT
<213> ORGANISM: Artificial Sequence
<220> FEATURE:
<223> OTHER INFORMATION: linker

<400> SEQUENCE: 7

Gly Ser Thr Ser Gly Ser Gly Lys Pro Gly Ser Gly Glu Gly Ser Thr
1               5                   10                  15

Lys Gly

<210> SEQ ID NO 8
<211> LENGTH: 63
<212> TYPE: DNA
<213> ORGANISM: Artificial Sequence
<220> FEATURE:
<223> OTHER INFORMATION: CD8 leader

<400> SEQUENCE: 8
atggccttac cagtgaccgc cttgctcctg ccgctggcct tgctgctcca cgccgccagg   60
ccg                                                                63

<210> SEQ ID NO 9
<211> LENGTH: 135
<212> TYPE: DNA
<213> ORGANISM: Artificial Sequence
<220> FEATURE:
<223> OTHER INFORMATION: CD8 hinge

<400> SEQUENCE: 9
accacgacgc cagcgccgcg accaccaaca ccggcgccca ccatcgcgtc gcagcccctg   60
tccctgcgcc cagaggcgtg ccggccagcg gcggggggcg cagtgcacac gagggggctg   120
gacttcgcct gtgat                                                   135

<210> SEQ ID NO 10
<211> LENGTH: 72
<212> TYPE: DNA
<213> ORGANISM: Artificial Sequence
<220> FEATURE:
<223> OTHER INFORMATION: CD8 transmembrane domain

<400> SEQUENCE: 10
atctacatct gggcgcccct ggccgggact tgtgggtcc ttctcctgtc actggttatc    60 acccttact gc                                                       72

<210> SEQ ID NO 11
<211> LENGTH: 126
<212> TYPE: DNA
<213> ORGANISM: Artificial Sequence
<220> FEATURE:
<223> OTHER INFORMATION: 4-1BB co-stimulatory domain
```

<400> SEQUENCE: 11

```
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                             126
```

<210> SEQ ID NO 12
<211> LENGTH: 342
<212> TYPE: DNA
<213> ORGANISM: Artificial Sequence
<220> FEATURE:
<223> OTHER INFORMATION: CD3 zeta

<400> SEQUENCE: 12

```
agagtgaagt tcagcaggag cgcagacgcc cccgcgtaca agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga aagataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgctaat ag                     342
```

<210> SEQ ID NO 13
<211> LENGTH: 6
<212> TYPE: DNA
<213> ORGANISM: Artificial Sequence
<220> FEATURE:
<223> OTHER INFORMATION: EcoRI restriction site

<400> SEQUENCE: 13

```
gaattc                                                               6
```

<210> SEQ ID NO 14
<211> LENGTH: 489
<212> TYPE: PRT
<213> ORGANISM: Artificial Sequence
<220> FEATURE:
<223> OTHER INFORMATION: CD19-4-1BB-CD3-CAR

<400> SEQUENCE: 14

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Lys Ala
    50                  55                  60

Pro Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Gly
            100                 105                 110

Asn Thr Leu Pro Tyr Thr Phe Gly Gly Gly Thr Lys Val Glu Ile Lys
        115                 120                 125

Gly Ser Thr Ser Gly Ser Gly Lys Pro Gly Ser Gly Glu Gly Ser Thr
    130                 135                 140
```

Lys Gly Gln Val Gln Leu Gln Glu Ser Gly Pro Gly Leu Val Lys Pro
145                 150                 155                 160

Ser Glu Thr Leu Ser Leu Thr Cys Thr Val Ser Gly Gly Ser Leu Pro
            165                 170                 175

Asp Tyr Gly Val Ser Trp Ile Arg Gln Pro Pro Gly Lys Gly Leu Glu
        180                 185                 190

Trp Ile Gly Val Ile Trp Gly Ser Glu Thr Thr Tyr Tyr Asn Ser Ala
    195                 200                 205

Leu Lys Ser Arg Val Thr Ile Ser Val Asp Thr Ser Lys Asn Gln Phe
210                 215                 220

Ser Leu Lys Leu Ser Ser Val Thr Ala Ala Asp Thr Ala Val Tyr Tyr
225                 230                 235                 240

Cys Ala Lys His Tyr Tyr Tyr Gly Gly Ser Tyr Ala Met Asp Tyr Trp
            245                 250                 255

Gly Gln Gly Thr Leu Val Thr Val Ser Ser Thr Thr Thr Pro Ala Pro
            260                 265                 270

Arg Pro Pro Thr Pro Ala Pro Thr Ile Ala Ser Gln Pro Leu Ser Leu
            275                 280                 285

Arg Pro Glu Ala Cys Arg Pro Ala Ala Gly Gly Ala Val His Thr Arg
290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
            325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
            355                 360                 365

Glu Glu Glu Glu Gly Gly Cys Glu Leu Arg Val Lys Phe Ser Arg Ser
        370                 375                 380

Ala Asp Ala Pro Ala Tyr Lys Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
            435                 440                 445

Ser Glu Ile Gly Met Lys Gly Glu Arg Arg Arg Gly Lys Gly His Asp
        450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
            485

<210> SEQ ID NO 15
<211> LENGTH: 735
<212> TYPE: DNA
<213> ORGANISM: Artificial Sequence
<220> FEATURE:
<223> OTHER INFORMATION: CD19 scFv

<400> SEQUENCE: 15
gatattcaga tgacccagag cccgagcagc ctgagcgcga gcgtgggcga tcgcgtgacc       60
attacctgcc gcgcgagcca ggatattagc aaatatctga actggtatca gcagaaaccg      120

-continued

```
ggcaaagcgc cgaaactgct gatttatcat accagccgcc tgcatagcgg cgtgccgagc    180
cgctttagcg gcagcggcag cggcaccgat tttaccctga ccattagcag cctgcagccg    240
gaagattttg cgacctatta ttgccagcag ggcaacaccc tgccgtatac ctttggcggc    300
ggcaccaaag tggaaattaa aggctccacc tctggatccg gcaagcccgg atctggcgag    360
ggatccacca agggccaggt gcagctgcag gaaagcggcc cgggcctggt gaaaccgagc    420
gaaaccctga gcctgacctg caccgtgagc ggcggcagcc tgccggatta tggcgtgagc    480
tggattcgcc agccgccggg caaaggcctg gaatggattg gcgtgatttg gggcagcgaa    540
accacctatt ataacagcgc gctgaaaagc cgcgtgacca ttagcgtgga taccagcaaa    600
aaccagttta gcctgaaact gagcagcgtg accgcggcgg ataccgcggt gtattattgc    660
gcgaaacatt attattatgg cggcagctat gcgatggatt attggggcca gggcaccctg    720
gtgaccgtga gcagc                                                     735
```

```
<210> SEQ ID NO 16
<211> LENGTH: 556
<212> TYPE: PRT
<213> ORGANISM: Homo sapiens

<400> SEQUENCE: 16
```

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255
```

```
Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
        290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
                340                 345                 350

Ser Leu Pro Thr Pro Thr Ser Gly Leu Gly Arg Ala Gln Arg Trp Ala
            355                 360                 365

Ala Gly Leu Gly Gly Thr Ala Pro Ser Tyr Gly Asn Pro Ser Ser Asp
            370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
            450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
            515                 520                 525

Asp Ser Tyr Glu Asn Met Asp Asn Pro Asp Gly Pro Asp Pro Ala Trp
            530                 535                 540

Gly Gly Gly Gly Arg Met Gly Thr Trp Ser Thr Arg
545                 550                 555
```

CAR-T CELLS WITH HUMANIZED CD19 SCFV WITH MUTATION IN CDR 1 REGION

RELATED APPLICATIONS

This application is a Continuation of International Patent Application Serial No. PCT/CN2019/109633, filed Sep. 30, 2019, which claims the benefit of priority under 35 U.S.C. § 119(e) to U.S. Application Ser. No. 62/773,112, filed Nov. 29, 2018. The entire contents of these applications are incorporated herein by reference.

FIELD OF THE INVENTION

The present invention relates to humanized CD19-CAR-T Cells that have CD19ScFv with mutation in CD19 ScFv VH CDR1 region (clone 11). The humanized CD19-CAR-T Cells of the present invention specifically decrease leukemia cell growth and are useful in the cell therapy for leukemia and lymphoma patients.

BACKGROUND OF THE INVENTION

Immunotherapy is emerging as a highly promising approach for the treatment of cancer. T cells or T lymphocytes, the armed forces of our immune system, constantly look for foreign antigens and discriminate abnormal (cancer or infected cells) from normal cells. Genetically modifying T cells with CAR (Chimeric antigen receptor) constructs is the most common approach to design tumor-specific T cells. CAR-T cells targeting tumor-associated antigens (TAA) can be infused into patients (called adoptive cell transfer or ACT) representing an efficient immunotherapy approach [1, 2]. The advantage of CAR-T technology compared with chemotherapy or antibody is that reprogrammed engineered T cells can proliferate and persist in the patient ("a living drug") [1, 3, 4].

CARs typically consist of a monoclonal antibody-derived single-chain variable fragment (scFv) at the N-terminal part, hinge, transmembrane domain and a number of intracellular co-activation domains: (i) CD28, (ii) CD137 (4-1BB), CD27, or other co-stimulatory domains, in tandem with an activation CD3-zeta domain. (FIG. 1) [1,2]. The evolution of CARs went from first generation (with no co-stimulation domains) to second generation (with one co-stimulation domain) to third generation CAR (with several co-stimulation domains). Generating CARs with two costimulatory domains (the so-called $3^{rd}$ generation CAR) have led to increased cytolytic CAR-T cell activity, improved persistence of CAR-T cells leading to its augmented antitumor activity. The structures of CAR is shown in FIG. 1. On the left panel—the structure of first generation (no costimulatory domains), on the middle panel-second generation (one co-stimulation domain CD28 or 4-BB) and on the right panel—third generation of CAR (two or several co-stimulation domains) are shown. The Figure is from Golubovskaya, Wu, *Cancers*, 2016[6].

There exists a need for an improved adoptive T cell immunotherapy with improved efficacy and reduced toxicities.

DETAILED DESCRIPTION OF THE INVENTION

The object of the present invention is humanized CD19-CAR-T Cells that have CD19ScFv with mutation.

In a first aspect of the invention, it provides a humanized single-chain variable fragment (scFv) of CD19 comprising VH having the amino acid sequence of SEQ ID NO: 6 and VL having the amino acid sequence of SEQ ID NO: 5.

In another preferred embodiment, the scFv comprises a linker in between VH and VL.

In another preferred embodiment, the scFv has the amino acid sequence of SEQ ID NO: 7.

In another preferred embodiment, the scFv has the amino acid sequence of SEQ ID NO: 4.

In a second aspect of the invention, it provides a chimeric antigen receptor (CAR) fusion protein comprising from N-terminus to C-terminus:

(i) the scFv of the first aspect of the invention,
(ii) a transmembrane domain,
(iii) at least one co-stimulatory domain, and
(Iv) an activating domain.

In another preferred embodiment, the chimeric antigen receptor fusion protein has the structure of formula I:

  (I)

wherein, each "-" is independently a linker or peptide bond;
L is an optional signal peptide sequence;
scFv is the scFv of the second aspect of the invention;
H is an optional hinge region;
TM is a transmembrane domain;
C is a co-stimulatory signaling molecule;
CD3ζ is a cytosolic signaling sequence derived from CD3ζ.

In another preferred embodiment, the L is a signal peptide of a protein selected from the group consisting of CD8, GM-CSF, CD4, CD137, or a combination thereof.

In another preferred embodiment, the L is a signal peptide derived from CD8.

In another preferred embodiment, the H is a hinge region of a protein selected from the group consisting of CD8, CD28, CD137, or a combination thereof.

In another preferred embodiment, the H is a hinge region derived from CD8.

In another preferred embodiment, the TM is a transmembrane region of a protein selected from the group consisting of CD28, CD3c, CD45, CD4, CD5, CD8, CD9, CD16, CD22, CD33, CD37, CD64, CD80, CD86, CD134, CD137, CD154, or a combination thereof.

In another preferred embodiment, the TM comprises a transmembrane region derived from CD8, and/or a transmembrane region derived from CD28.

In another preferred embodiment, the C is a co-stimulatory signaling molecule of a protein selected from the group consisting of OX40, CD2, CD7, CD27, CD28, CD30, CD40, CD70, CD134, 4-1BB (CD137), PD1, Dap10, CDS, ICAM-1, LFA-1 (CD11a/CD18), ICOS (CD278), NKG2D, GITR, TLR2, or a combination thereof.

In another preferred embodiment, C comprises a co-stimulatory signaling molecule derived from 4-1BB, and/or a co-stimulatory signaling molecule derived from CD28.

In another preferred embodiment, the CAR fusion protein has the amino acid sequence of SEQ ID NO: 14.

In the third aspect of the invention, it provides an antibody against human CD19 comprising VH having the amino acid sequence of SEQ ID NO: 6 and VL having the amino acid sequence of SEQ ID NO: 5.

In another preferred embodiment, the antibody binds to human CD19 protein.

In another preferred embodiment, the antibody is selected from the group consisting of an animal-derived antibody, a chimeric antibody, a humanized antibody, or a combination thereof.

In another preferred embodiment, the antibody is a double chain antibody or a single chain antibody.

In another preferred embodiment, the antibody is a monoclonal antibody.

In a fourth aspect of the invention, a recombinant protein is provided, which has:
(I) the scFv according to the first aspect of the invention, or the antibody according to the third aspect of the invention;
(Ii) optional tag sequence that facilitate expression and/or purification.

In another preferred embodiment, the tag sequence comprises a 6His tag.

In another preferred embodiment, the recombinant protein (or polypeptide) comprises fusion protein.

In another preferred embodiment, the recombinant protein is a monomer, a dimer, or a multimer.

In a fifth aspect of the invention, an antibody drug conjugate is provided, which comprises:
(a) the scFv according to the first aspect of the invention, or the antibody according to the third aspect of the invention;
(b) a coupling moiety coupled to the antibody moiety, and the coupling moiety is selected from the group consisting of a detectable label, a drug, a toxin, a cytokine, a radionuclide, an enzyme, or a combination thereof.

In another preferred embodiment, the antibody moiety is coupled to the coupling moiety via a chemical bond or linker.

In the sixth aspect of the invention, it provides a nucleic acid molecule encoding the scFv of the first aspect of the invention or the CAR fusion protein of the second aspect of the invention, or the antibody of the third aspect of the invention.

In another preferred embodiment, the nucleic acid molecule encodes the scFv according to the first aspect of the invention, and has the nucleic acid sequence of SEQ ID NO.: 1 encoding VL and the nucleic acid sequence of SEQ ID NO.: 2 coding VH.

In the seventh aspect of the invention, it provides a vector comprising the nucleic acid molecule of the sixth aspect of the invention.

In another preferred embodiment, the vector is selected from the group consisting of DNA, RNA, plasmid, lentiviral vector, adenoviral vector, retroviral vector, transposon, or a combination thereof.

In another preferred embodiment, the vector is a lentiviral vector.

In the eighth aspect of the invention, it provides a host cell comprising the vector of the seventh aspect of the invention, or in which an exogenous nucleic acid molecule of the sixth aspect of the invention is integrated in chromosome, or expressing the scFv of the first aspect of the invention, the CAR fusion protein of the second aspect of the invention or the antibody of the third aspect of the invention.

In another preferred embodiment, the cell is an isolated cell, and/or the cell is a genetically engineered cell.

In another preferred embodiment, the cell is a mammalian cell.

In another preferred embodiment, the cell is a T cell.

In another preferred embodiment, the host cell is an engineered immune cell.

In another preferred embodiment, the engineered immune cell comprise T cell or NK cell, preferably is (i) chimeric antigen receptor T cell (CAR-T cell); or (ii) chimeric antigen receptor NK cell (CAR-NK cell).

In a ninth aspect of the invention, a method for preparing an engineered immune cell is provided, wherein the engineered immune cell expresses the chimeric antigen receptor fusion protein according to the second aspect of the invention, the method comprises steps: introducing the nucleic acid molecule of the sixth aspect of the invention or the vector of the seventh aspect of the invention into a T cell or an NK cell, thereby obtaining the engineered immune cell.

In another preferred embodiment, the method further comprises the step of detecting the function and effectiveness of the obtained engineered immune cell.

In the tenth aspect of the invention, it provides a formulation comprising the scFv of the first aspect of the invention, or the CAR fusion protein of the second aspect of the invention, or the vector of the seventh aspect of the invention, or the cell of the eighth aspect of the invention, and a pharmaceutically acceptable carrier, diluent or excipient.

In an eleventh aspect of the invention, there is provided a use of the scFv of the first aspect of the invention, the CAR fusion protein of the second aspect of the invention, the antibody of the third aspect of the invention, the recombinant protein of the fourth aspect of the invention, the antibody drug conjugate of the fifth aspect of the invention, or the cell of the eighth aspect of the invention, for the preparation of a medicament or a formulation for preventing and/or treating cancer or a tumor.

In another preferred embodiment, the tumor is selected from the group consisting of a hematological tumor, a solid tumor, or a combination thereof.

In another preferred embodiment, the blood tumor is selected from the group consisting of acute myeloid leukemia (AML), multiple myeloma (MM), chronic lymphocytic leukemia (CLL), acute lymphoblastic leukemia (ALL), diffuse large B cell lymphoma (DLBCL), or a combination thereof.

In another preferred embodiment, the solid tumor is selected from the group consisting of gastric cancer, peritoneal metastasis of gastric cancer, liver cancer, renal cancer, lung cancer, small intestine cancer, bone cancer, prostate cancer, colorectal cancer, breast cancer, cervical cancer, ovarian cancer, lymphoma, nasopharyngeal carcinoma, adrenal tumor, bladder tumor, non-small cell lung cancer (NSCLC), glioma, endometrial cancer, testicular cancer, urinary tract tumor, thyroid cancer, or a combination thereof.

In another preferred embodiment, the solid tumor is selected from the group consisting of ovarian cancer, mesothelioma, lung cancer, pancreatic cancer, breast cancer, liver cancer, endometrial cancer, or a combination thereof.

In a twelfth aspect of the invention, a kit for the preparation of the cell according to the eighth aspect of the invention is provided, the kit comprises a container and the nucleic acid molecule of the sixth aspect of the invention or the vector of the seventh aspect of the invention is located in the container.

In a thirteenth aspect of the invention, the use of the cell of the eighth aspect of the invention, or the formulation of the tenth aspect of the invention is provided, for the prevention and/or treatment of cancer or tumor.

In a fourteenth aspect of the invention, there is provided a method of treating a disease comprising administering an appropriate amount of the cell of the eighth aspect of the invention, or the formulation of the tenth aspect of the invention, to a subject in need of treatment.

In another preferred embodiment, the disease is cancer or tumor.

It is to be understood that the various technical features of the present invention mentioned above and the various technical features specifically described hereinafter (as in the Examples) may be combined with each other within the scope of the present invention to constitute a new or preferred technical solution, which will not be repeated one by one herein.

DEFINITIONS

Figure 1:
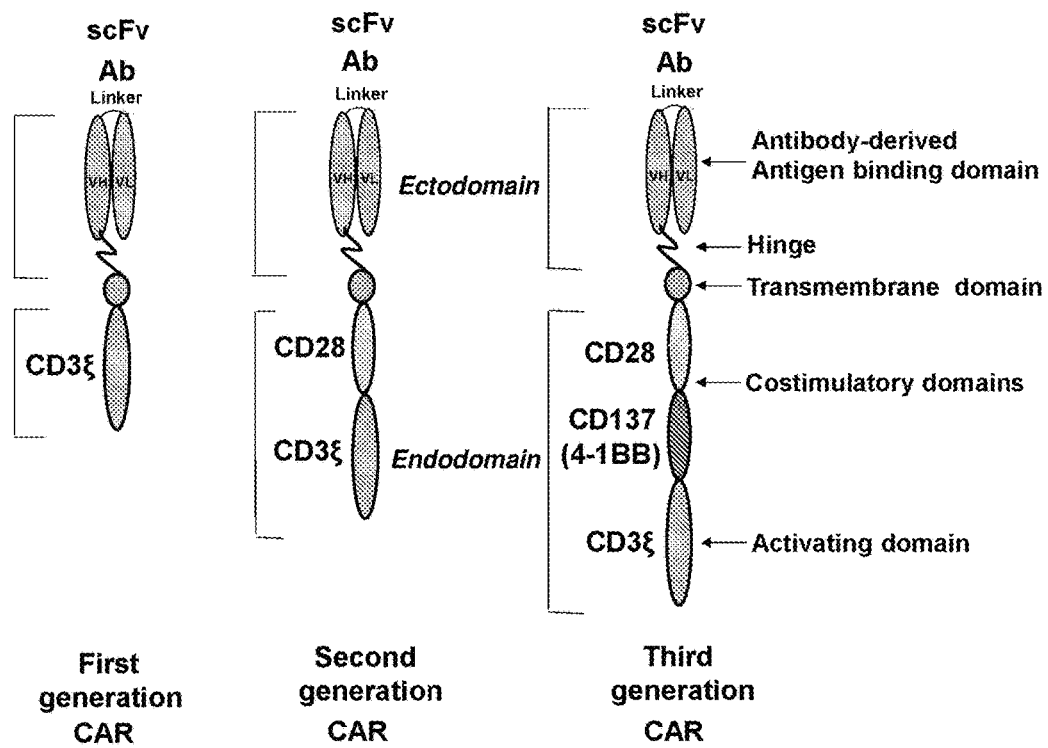
FIG. 1. The structures of CAR

As used herein, a "chimeric antigen receptor (CAR)" means a fused protein comprising an extracellular domain capable of binding to an antigen, a transmembrane domain derived from a polypeptide different from a polypeptide from which the extracellular domain is derived, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell.

"CDR"s are complementary-determining Regions of VH or VL chains of antibody which are critical for binding with antigen.

As used herein, "humanized antibodies" are antibodies from non-human species whose protein sequences have been modified to increase their similarity to antibody variants produced naturally in humans.

As used herein, a "domain" means one region in a polypeptide which is folded into a particular structure independently of other regions.

As used herein, a "single chain variable fragment (scFv)" means a single chain polypeptide derived from an antibody which retains the ability to bind to an antigen. An example of the scFv includes an antibody polypeptide which is formed by a recombinant DNA technique and in which Fv regions of immunoglobulin heavy chain (H chain) and light chain (L chain) fragments are linked via a spacer sequence. Various methods for engineering a scFv are known to a person skilled in the art.

As used herein, a "tumor antigen" means a biological molecule having antigenicity, expression of which causes cancer.

CD19

CD19 is a B-cell type lymphocyte antigen which is expressed on all B-cell malignancies, including acute lymphoblastic leukemia (ALL), chronic lymphoblastic leukemia (CLL), and Non-Hodgkin lymphomas. This universal expression among leukemia and lymphomas made this antigen an attractive target for targeting with CAR-T cells [3].

CD19 Structure and Signaling

The human CD19 protein is a 95 kDa transmembrane glycoprotein which consists of 556 amino-acids: 20-291-extracellular domain; 292-313-transmembrane domain; 314-556-cytoplasmic domain as shown below (extracellular domain underlined). It belongs to immunoglobulin superfamily proteins and mediates B cell receptor, BCR-dependent and independent signaling. CD19 binds to BCR and other cell surface protein to modulate intracellular signaling through binding other kinases and binding partners. CD19 signaling is connected with Src-family kinase, PI3Kinase, Abl, AKT-dependent signaling. CD19 is a biomarker of B-cells mediating survival signaling and immune responses.

```
                                          (SEQ ID NO.: 16)
         10         20         30         40
MPPPRLLFFL LFLTPMEVRP EEPLVVKVEE GDNAVLQCLK 50         60         70         80
GTSDGPTQQL TWSRESPLKP FLKLSLGLPG LGIHMRPLAI 90        100        110        120
WLYIENVSQQ MGGFYLCQPG PPSEKAWQPG WTVNVEGSGE 130        140        150        160
LFRWNVSDLG GLGCGLKNRS SEGPSSPSGK LMSPKLYVWA 170        180        190        200
KDRPEIWEGE PPCLPPRDSL NQSLSQDLTM APGSTLWLSC 210        220        230        240
GVPPDSVSRG PLSWTHVHPK GPKSLLSLEL KDDRPARDMW 250        260        270        280
VMETGLLLPR ATAQDAGKYY CHRGNLTMSF HLEITARPVL 290        300        310        320
WHWLLRTGGW KVSAVILAYL IFCLCSLVGI LHLQRALVLR 330        340        350        360
RKRKRMTDPT RRFFKVTPPP GSGPQNQYGN VLSLPTPTSG
```

```
            370         380         390         400
         LGRAQRWAAG  LGGTAPSYGN  PSSDVQADGA  LGSRSPPGVG 410         420         430         440
         PEEEEGEGYE  EPDSEEDSEF  YENDSNLGQD  QLSQDGSGYE 450         460         470         480
         NPEDEPLGPE  DEDSFSNAES  YENEDEELIQ  PVARTMDFLS 490         500         510         520
         PHGSAWDPSR  EATSLGSQSY  EDMRGILYAA  PQLRSIRGQP 530         540         550
         GPNHEEDADS  YENMDNPDGP  DPAWGGGGRM  GTWSTR
```

Mutated CD19 scFv of the Present Invention

The inventors have generated humanized CD19 scFv containing a mutation in CDR region of VH (V27G) and generated CAR-T cells based on the humanized CD19 ScFv sequence containing this mutation specifically targeting CD19. The inventors have produced the humanized CD19-CAR-T cells to target cancer cells overexpressing CD19 antigen. The humanized CD19-CAR-T cells of the present invention secreted high level of IFN-gamma against leukemia cancer cells and killed Hela-CD19-positive target cells but not control Hela cells.

The present invention is directed to a humanized antihuman CD19 antibody from mouse clone FMC63, comprising humanized $V_H$ having the amino acid of SEQ ID NO: 6 and humanized $V_L$ having the amino acid of SEQ ID NO: 5, respectively. In one embodiment, the humanized anti-human CD19 antibody is a single-chain variable fragment (scFv).

The present invention is also directed to a chimeric antigen receptor fusion protein comprising from N-terminus to C-terminus: (i) a single-chain variable fragment (scFv) against CD19 (the present invention), (ii) a transmembrane domain, (iii) at least one co-stimulatory domains, and (iv) an activating domain.

Figure 2:
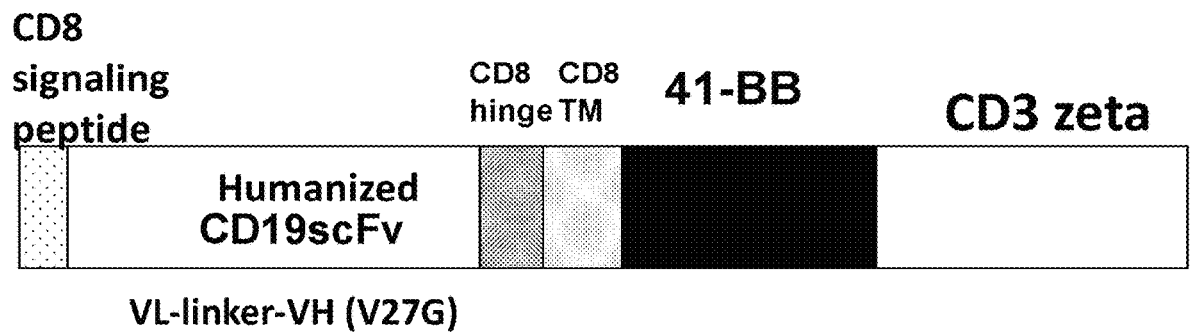
FIG. 2. The structure of humanized CD19-CAR construct.

FIG. 2 shows the structure of humanized CD19 CAR construct. The humanized CD19 scFv (clone 11) containing mutation V27G in CDR1 region of VH is shown. The second generation CD19-CAR was used.

The inventors have generated humanized CD19-ScFv with mutation V27G in CDR1 region of CD19 scFv, and used this humanized CD19-ScFv for CAR generation to produce CD19-41BB-CD3-CAR-T (hCD19-CAR-T) cells against leukemia cells. The humanized CD19-CAR-T cells of the present invention secreted high levels of IFN-gamma, were positive by cytotoxicity assay with Hela-CD19 cells but not with Hela cells, which indicates specific killing activity of CAR-T cells against target cancer cells with CD19 overexpression.

The advantages of the humanized CD19-ScFv of the present invention vs. mouse CD19-ScFv include less immunogenicity to human due to humanized CD19 scFv. Thus, the humanized CD19-CAR-T cells are advantageous as therapeutic agents in many clinical applications.

The advantages of the humanized CD19-ScFv of the present invention, which includes a mutation in CDR1 of VH (V27G in VH), vs. humanized CD19-ScFv without a mutation include prolonged survival in mice treated with mutated humanized CD19-CAR T cells.

The present humanized CD19 ScFv can be used for immunotherapy applications: toxin/drug-conjugated antibody, monoclonal therapeutic antibody, and CAR-T cell immunotherapy.

Humanized CD19-CAR-T cells using the present humanized CD19 ScFv effectively target CD19 antigen in CD19-positive cancer cell lines.

Humanized CD19-CAR-T cells can be used in combination with different chemotherapy: checkpoint inhibitors, targeted therapies, small molecule inhibitors, and antibodies.

Humanized CD19-CAR-T cells can be used clinically for CD19-positive cancer cells.

Modifications of co-activation domains: CD28, 4-1BB and others can be used to increase its efficacy. Tag-conjugated humanized CD19 scFv can be used for CAR generation.

Humanized CD19-CAR-T cells can be used with different safety switches: t-EGFR, RQR (Rituximab-CD34-Rituximab), inducible caspase-9 and other.

Third generation CAR-T or other co-activation signaling domains can be used for the same humanized CD19-scFv inside CAR.

The humanized CD19 CAR can be combined with CARs targeting other tumor antigens or tumor microenvironment, e.g., VEGFR-1-3, PDL-1, bi-specific antibodies with CD19 and CD3 or other antigens can be generated for therapy.

The humanized CD19-CAR-T cells can be used against cancer stem cells or tumor initiating cells that are most resistant against chemotherapy and form aggressive tumors.

Vector

The invention also provides a DNA construct encoding the CAR sequences of the invention.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically.

The present invention also provides vectors in which the DNA construct of the present invention is inserted. Vectors derived from retroviruses such as the lentivirus are suitable tools to achieve long-term gene transfer since they allow long-term, stable integration of a transgene and its propagation in daughter cells. Lentiviral vectors have the advantage over vectors derived from onco-retroviruses such as murine leukemia viruses in that they can transduce non-proliferating cells, such as hepatocytes. They also have the advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration in eukaryotes. Typical cloning vectors contain transcription and translation terminators, initiation sequences, and promoters useful for regulation of the expression of the desired nucleic acid sequence.

The expression constructs of the present invention may also be used for nucleic acid immune and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector, The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors, Further, the expression vector may be provided to a cell in the form of a viral vector. Viral vector technology is well known in the art and is described, for example, in Sambrook et al, (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters, inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionein promoter, a glucocorticoid promoter, a progesterone promoter, and a tetracycline promoter.

In order to assess the expression of a CAR polypeptide or portions thereof, the expression vector to be introduced into a ceil can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

In the case where a non-viral delivery system is utilized, genome editing technique is exemplarily employed to complete the invention, for example CRISPR-Cas9, ZFN or TALEN.

In a preferred embodiment of the invention, the vector is a lentiviral vector.

In a preferred embodiment of the invention, the DNA construct further comprises a signal peptide coding sequence. Preferably, the signal peptide sequence is ligated upstream of the nucleic acid sequence of antigen binding domain.

Therapeutic Application

The present invention encompasses a cell (e.g., T cell) transduced with a lentiviral vector (LV) encoding the CAR of the invention. The transduced T cell can elicit a CAR-mediated T-cell response.

Thus, the present invention also provides a method for stimulating a T cell-mediated immune response to a target cell population or tissue in a mammal comprising the step of administering to the mammal a T cell that expresses the CAR of the invention.

In one embodiment, the present invention includes a type of cellular therapy where T cells are genetically modified to express the CAR of the invention and the CAR-T cell is infused to a recipient in need thereof. The infused cell is able to kill tumor cells in the recipient. Unlike antibody therapies, CAR-T cells are able to replicate in vivo resulting in long-term persistence that can lead to sustained tumor control.

In one embodiment, the CAR-T cells of the invention can undergo robust in vivo T cell expansion and can persist for an extended amount of time. In addition, the CAR mediated immune response may be part of an adoptive immunotherapy approach in which CAR-modified T cells induce an immune response specific to the antigen binding moiety in the CAR. For example, an anti-CD19 CAR-T cell elicits an immune response specific against cells expressing CD19.

Although the data disclosed herein specifically disclose lentiviral vector comprising anti-CD19 scFv, hinge and transmembrane domain, and 4-1BB and CD3t signaling domains, the invention should be construed to include any number of variations for each of the components of the construct as described elsewhere herein.

Adaptation diseases that may be treated include CD19 positive tumors and diseases caused by excessive B cells. CD19 positive tumors may include CD19 positive non-solid tumors (such as hematological tumors, for example, leukemias and lymphomas) or solid tumors. Types of tumors or cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblasts, promyeiocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, mesothelioma, malignant lymphoma, pancreatic cancer and ovarian cancer.

The CAR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of CCL. In certain embodiments, the cells of the invention are used in the treatment of patients at risk for developing CCL. Thus, the present invention provides methods for the treatment or prevention of CCL comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2, IL-17 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an antitumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al, New Eng. J. of Med. 319: 1676, 1988). The optimal dosage and treatment regime for a particular patient can readily be determined by one skilled in the art of medicine by monitoring the patient for signs of disease and adjusting the treatment accordingly.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunotherapeutic agents. In a further embodiment, the cell compositions of the present invention are administered to a patient in conjunction with (e.g., before, simultaneously or following) bone marrow transplantation, or the use of chemotherapy agents such as, fludarabine, external-beam radiation therapy (XRT), cyclophosphamide. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. In general, $1\times10^6$ to $1\times10^{10}$ of the modified T cells of the invention (e.g., CAR-T 19 cells) can be applied to patients by means of, for example, intravenous infusion each treatment or each course of treatment.

The following examples further illustrate the present invention. These examples are intended merely to be illustrative of the present invention and are not to be construed as being limiting.

EXAMPLES

The inventors generated humanized CD19-ScFv-CAR constructs inside lentiviral vector cloned into Xba I and Eco R I sites of lentiviral vector. pCD510-FMC63-28z lentiviral CAR construct containing the humanized CD19 ScFv-41BB-CD3zeta insert—between the Xba I and Eco RI cloning sites.

The lentiviruses were generated in 293T cells and titer was established by RT-PCR. Then equal dose of lentiviruses was used for transduction of T cells.

Example 1. Humanized CD19 Antibody: VH and VL and scFv Sequences

The inventors have humanized CD19 scFv from mouse CD19 FMC63 scFv clone, and selected a humanized scFv with a mutation in CDR1 (Clone 11) based on the in vivo data efficacy. The structure of humanized CD19 scFv is: VL-linker-VH. Linker is G S T S G S G K P G S G E G S T K G (SEQ ID NO: 7).

The bold highlights the nucleotide sequence of humanized CD19 $V_L$ (SEQ ID NO: 1); the regular font highlights the nucleotide sequence of $V_H$ (SEQ ID NO: 2, bold mark mutation (ggc) coding G); in between (italicized, smaller font) is the nucleotide sequence (SEQ ID NO: 3) encoding linker G S T S G S G K P G S G G S T K G (SEQ ID NO: 7)

(SEQ ID NO.: 15)
gatattcagatgacccagagcccgagcagcctgagcgcgagcgtggcga tcgcgtgaccattacctgcgcgcgagccaggatattagcaaatatctga actggtatcagcagaaaccgggcaaagcgccgaaactgctgatttatcat accagccgcctgcatagcggcgtgccgagccgctttagcggcagcggcag cggcaccgatttttaccctgaccattagcagcctgcagccggaagattttg

```
cgacctattattgccagcagggcaacaccctgccgtatacctttggcggc ggcaccaaagtggaaattaaaggctccacctctggatccggcaagcccgg atctggcgagggatccaccaagggccaggtgcagctgcaggaaagcggcc cgggcctggtgaaaccgagcgaaaccctgagcctgacctgcaccgtgagc ggcggcagcctgccggattatggcgtgagctggattcgccagccgccggg caaaggcctggaatggattggcgtgatttggggcagcgaaaccacctatt ataacagcgcgctgaaaagccgcgtgaccattagcgtggataccagcaaa aaccagtttagcctgaaactgagcagcgtgaccgcggcggataccgcggt gtattattgcgcgaaacattattattatggcggcagctatgcgatggatt attggggccagggcaccctggtgaccgtgagcagc
```

Humanized CD19 scFv (SEQ ID NO: 4): bold VL, regular font VH, CDR regions underlined, the mutation is at amino acid position 27 of VH (SEQ ID NO: 6), which is shown as a bigger italic font G (V27G of VH)

(SEQ ID NO.: 4)
DIQMTQSPSSLSASVGDRVTITCRASQDISKYLNWYQQKPGKAPKLLIYH

TSRLHSGVPSRFSGSCSGTDFTLTISSLQPEDFATYYCQQGNTLPYTEGG

GTKVEIK

*GSTSGSGKPGSGEGSTKG*

QVQLQESGPGLVKPSETLSLTCTV*G* SLPDYGVSWIRQPPGKGLEWKIGV

IWGSETTYYNSALKSRVTISVDTSKNQFSLKLSSVTAADTAVYYCAKHYY

YGGSYAMDYWGQGTLVTVSS

In the protein, the bold highlights the amino acid sequence of $V_L$ (SEQ ID NO: 5); the regular not italics font highlights the amino sequence of $V_H$ (SEQ ID NO: 6); in between italicized, smaller font is the amino acid sequence of linker sequence (SEQ ID NO: 7).

Figure 3:
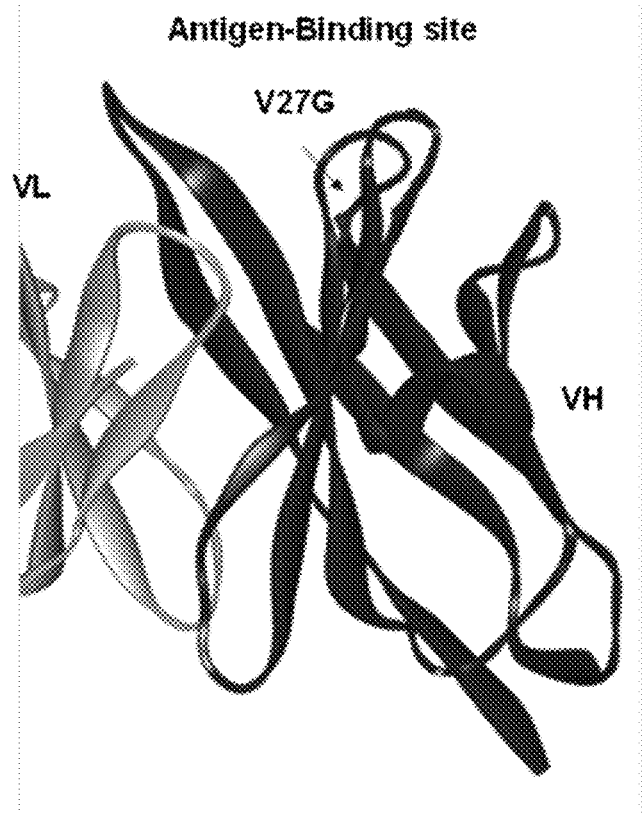
FIG. 3. The model of humanized CD19 with mutation in CDR 1 domain (V27G).

By 3D-modeling and binding experiments, the inventors have discovered that mutation in CDR1 region of VH in humanized CD19 antibody can improve the binding of the antibody with CD19 antigen. The mutation in clone 11, CDR1, V27G of VH is shown in FIG. 3.

Example 2. Humanized CD19-CAR Sequences

The scheme of Humanized CD19-CAR construct is shown on FIG. 2. Lentiviral vector with EF1a promoter was used for cloning of humanized scFv CAR sequences.

The following nucleotide sequence shows CD8 leader-Humanized CD19 ScFv-CD8 hinge-TM8-41BB-CD3 zeta of the present invention. The CAR structure includes Human CD8 signaling peptide, humanized CD19 scFv ($V_L$-Linker-$V_H$), CD8 hinge, CD8 trans-membrane, 41BB co-stimulatory and CD3 zeta activation domains (FIG. 2).

CD8 leader sequence-CD19 scFv ($V_L$-Linker-$V_H$)-CD8 hinge CD8 TM-41BB-CD3-zeta:

```
<CD8 leader>
                                            (SEQ ID NO.: 8)
ATGGCCTTACCAGTGACCGCCTTGCTCCTGCCGCTGGCCTTGCTGCTCCACGCCGCCAGGCCG <Humanized CD19 (VL-linker-VH), clone 11 scFv> (mutation
ggc which codes V27G is shown in bold)
                                            (SEQ ID NO.: 15)
gatattcagatgacccagagcccgagcagcctgagcgcgagcgtgggcgatcgcgtgacc attacctgccgcgcgagccaggatattagcaaatatctgaactggtatcagcagaaaccg ggcaaagcgccgaaactgctgatttatcataccagccgcctgcatagcggcgtgccgagc cgctttagcggcagcggcagcggcaccgatttta ccctgaccattagcagcctgcagccg gaagattttgcgacctattattgccagcagggcaacaccctgccgtatacctttggcggc ggcaccaaagtggaaattaaa ggctccacctctggatccggcaagcccggatctggcgagggatccaccaagggc caggtgcagctgcaggaaagcggcccgggcctggtgaaaccgagcgaaaccctgagcctg acctgcaccgtgagcggcggcagcctgccggattatggcgtgagctggattcgccagccg ccgggcaaaggcctggaatggattggcgtgatttggggcagcgaaaccacctattataac agcgcgctgaaaagccgcgtgaccattagcgtggataccagcaaaaaccagtttagcctg aaactgagcagcgtgaccgcggcggataccgcggtgtattattgcgcgaaacattattat tatggcggcagctatgcgatggattattggggccagggcaccctggtgaccgtgagcagc <CD8 hinge>
                                            (SEQ ID NO.: 9)
ACCACGACGCCAGCGCCGCGACCACCAACACCGGCGCCCACCATCGCGTCGCAGCCCC

TGTCCCTGCGCCCAGAGGCGTGCCGGCCAGCGGCGGGGGCGCAGTGCACACGAGGG

GGCTGGACTTCGCCTGTGAT
```

```
<CD8 TM>
                                                     (SEQ ID NO.: 10)
ATCTACATCTGGGCGCCCCTGGCCGGGACTTGTGGGGTCCTTCTCCTGTCACTGGTTAT

CACCCTTTACTGC

<4-1BB co-stimulatory domain>
                                                     (SEQ ID NO.: 11)
AAACGGGGCAGAAAGAAACTCCTGTATATATTCAAACAACCATTTATGAGACCAGTAC

AAACTACTCAAGAGGAAGATGGCTGTAGCTGCCGATTTCCAGAAGAAGAAGAAGGAG

GATGTGAACTG

<CD3 zeta>
                                                     (SEQ ID NO.: 12)
AGAGTGAAGTTCAGCAGGAGCGCAGACGCCCCCGCGTACAAGCAGGGCCAGAACCAG

CTCTATAACGAGCTCAATCTAGGACGAAGAGAGGAGTACGATGTTTTGGACAAGAGAC

GTGGCCGGGACCCTGAGATGGGGGGAAAGCCGAGAAGGAAGAACCCTCAGGAAGGCC

TGTACAATGAACTGCAGAAAGATAAGATGGCGGAGGCCTACAGTGAGATTGGGATGA

AAGGCGAGCGCCGGAGGGGCAAGGGGCACGATGGCCTTTACCAGGGTCTCAGTACAG

CCACCAAGGACACCTACGACGCCCTTCACATGCAGGCCCTGCCCCCTCGCTAATAG

<EcoRI restriction site>
                                                     (SEQ ID NO.: 13)
gaattc
```

Translated amino-acid sequence of humanized CD19-4-1BB-CD3-CAR protein (see FIG. 3 for construct structure), mutation in CDR1 VH is shown in bold, underlined:

```
                                       (SEQ ID NO.: 14)
M A L P V T A L L L P L A L L L H A A R P D I

Q M T Q S P S S L S A S V G D R V T I T C R A

S Q D I S K Y L N W Y Q Q K P G K A P K L L I

Y H T S R L H S G V P S R F S G S G S G T D F

T L T I S S L Q P E D F A T Y Y C Q Q G N T L

P Y T F G G G T K V E I K G S T S G S G K P G

S G E G S T K G Q V Q L Q E S G P G L V K P S

E T L S L T C T V S G G SLPDYGVSWIR

Q P P G K G L E W I G V I W G S E T T Y Y N S

A L K S R V T I S V D T S K N Q F S L K L S S

V T A A D T A V Y Y C A K H Y Y Y G G S Y A M

D Y W G Q G T L V T V S S T T T P A P R P P T

P A P T I A S Q P L S L R P E A C R P A A G G

A V H T R G L D F A C D I Y I W A P L A G T C

G V L L L S L V I T L Y C K R G R K K L L Y I

F K Q P F M R P V Q T T Q E E D G C S R F P E

E E E G G C E L R V K F S R S A D A P A Y K Q

G Q N Q L Y N E L N L G R R E E Y D V L D K R

R G R D P E M G G K P R R K N P Q E G L Y N E

L Q K D K M A E A Y S E I G M K G E R R R G K

G H D G L Y Q G L S T A T K D T Y D A L H M Q

A L P P R
```

Example 3. Humanized CD19-CAR-T Cells Kill Leukemia Cells and Secrete IFN-Gamma Against CD19-Positive Cancer Cells We designed humanized CD19-CAR-T cells with humanized CD19-CAR construct shown in FIG. 2. We used Mock ScFv with unrelated ScFv and generated Mock-CAR-T cells as a negative control. Humanized CD19-CAR-T cells expressed CD19 ScFv as detected by FACS.

Figure 4:
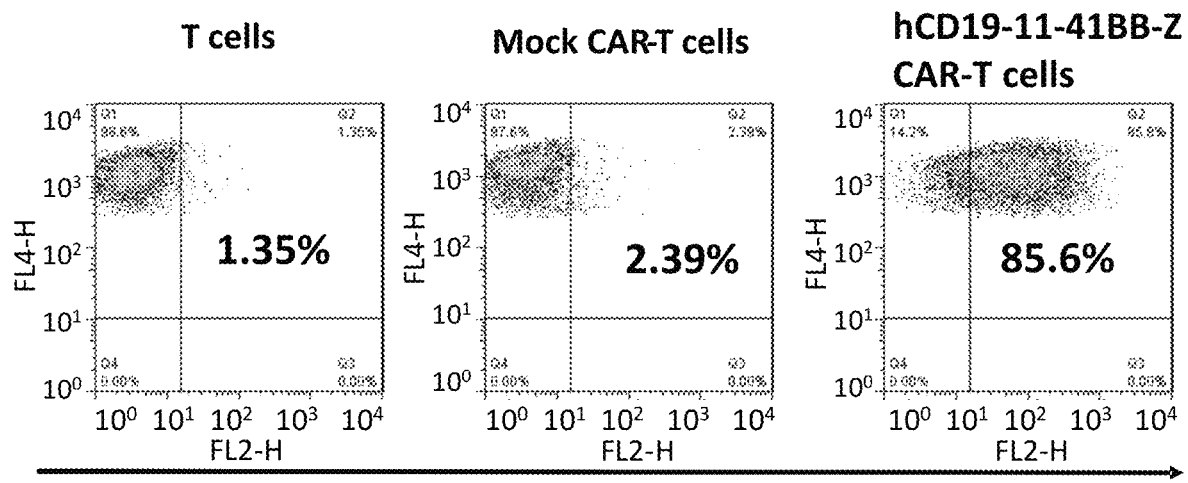
FIG. 4. Humanized CD19-CAR construct was detected by FACS analysis with human FAB antibody by FACS.

The result was shown in FIG. 4. Humanized CD19-CAR construct was detected by FACS with human FAB antibody. Humanized CD19-CAR-positive cells were detected after transduction of lentiviral humanized CD19 CAR into T cells. CD3Z shows CD3 zeta activation domain.

Example 4. Humanized CD19-CAR-T Cells Killed Hela-CD19 Cells but not Hela Cells We incubated humanized effector CD19-CAR-T cells of the present invention with target Hela-CD19 target cells and also Hela (CD19-negative) control cells and performed real-time cytotoxicity assay (RTCA, as described in [4]).

Figure 5:
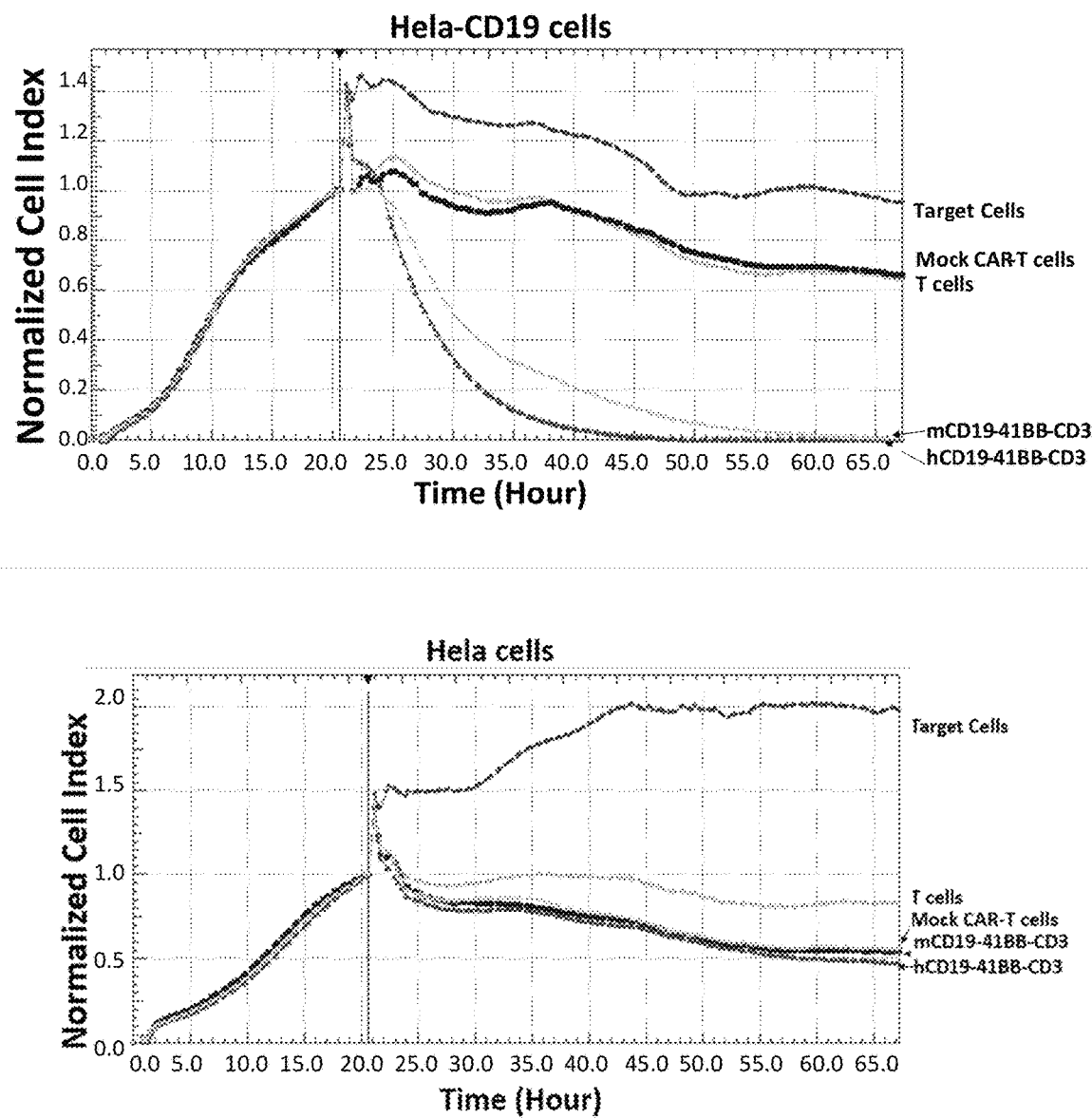
FIG. 5. Humanized CD19-CAR-T cells killed Hela-CD19 cells but not Hela cells.

The result was shown in FIG. 5. Humanized CD19-CAR-T cells specifically killed Hela-CD19 cells as the number of target cell (cell index) significantly decreased by CAR-T cells versus T cells and Mock CAR-T cells (FIG. 5, upper panel). Humanized CD19-CAR-T cells did not kill CD19-negative Hela cells, and there was no significant difference between T cells, Mock and CAR-T cells in killing CD19-negative Hela cells (FIG. 5, lower panel). This demonstrate high specificity of humanized CD19-CAR-T cells to target CD19 antigen and to kill only CD19-positive cells but not CD19-negative Hela cells (FIG. 5).

xCELLigence Real-Time Cytotoxicity Assay was used for detection of humanized CD19-CAR-T and mouse CD19-41BB-CD3 CAR-T cell cytotoxicity, as described [4]. Normalized cell index is shown on Y-axis, and time in hours is shown on X-axis. From top to bottom on the right, Target cells alone; then effector cells added to target cells: T cells; Mock CAR-T cells; Mouse Cd19-CAR-T cells; Humanized CD19 CAR-T cells.

Example 5. Humanized CD19 CAR-T Cells Secrete IFN-Gamma Against Target Hela-CD19 Cells We collected supernatant after co-incubation of humanized CD19-CAR-T cells and target Hela-CD19 and performed IFN-gamma assay, as described [5].

Figure 6:
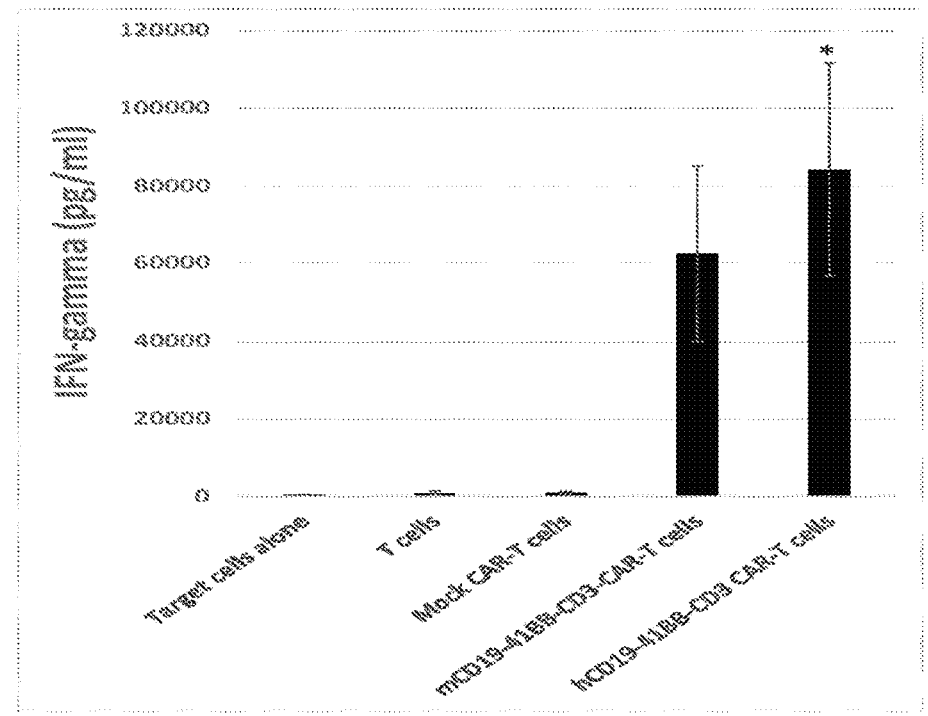
FIG. 6. Humanized CD19-CAR-T cells secreted IFN-gamma with Hela-CD19-positive cells. *, p<0.05, IFN-gamma secreted by humanized CAR-T cells versus mouse CD19-CAR-T cells, T cells, Mock CAR-T cells in Hela-CD19 cells.

The result was shown in FIG. 6. Humanized CD19-CAR-T cells secreted IFN-gamma with Hela-CD19 significantly higher than T cells and Mock CAR-T cells. The level of IFN-gamma secreted by humanized CD19-CAR-T cells was significantly higher than by mouse CD19-CAR-T cells ($p<0.05$) suggesting higher activity of humanized CD19-CAR-T cells versus CD19-positive target cells.

Example 6. Humanized CD19-CAR-T Cells Decrease Raji Xenograft Tumor Growth In Vivo We injected Raji-luciferase-positive cells into NSG-mice intravenously and then next day injected $1 \times 10^7$ humanized CD19-CAR-T cells, as described [4]. We used IVIS system to detect Raji xenograft tumor cell growth by imaging.

Figure 7:
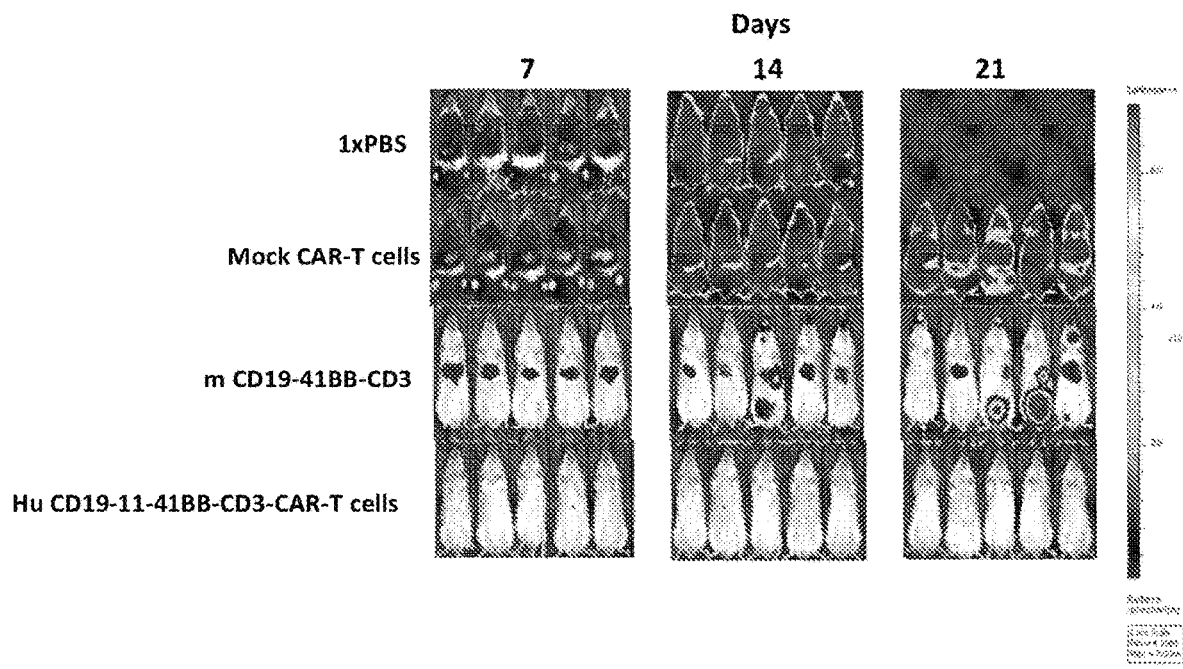
FIG. 7. Humanized CD19-CAR-T cells significantly decreased mouse xenograft tumor growth by imaging.

The result was shown in FIG. 7. Humanized CD19-CAR-T cells significantly decreased Raji xenograft growth by imaging compared to control untreated and Mock-CAR-T cells. The decreased Raji tumor growth was more pronounced with humanized CAR-T cells than with mouse CD19-CAR-T cells.

Figure 8:
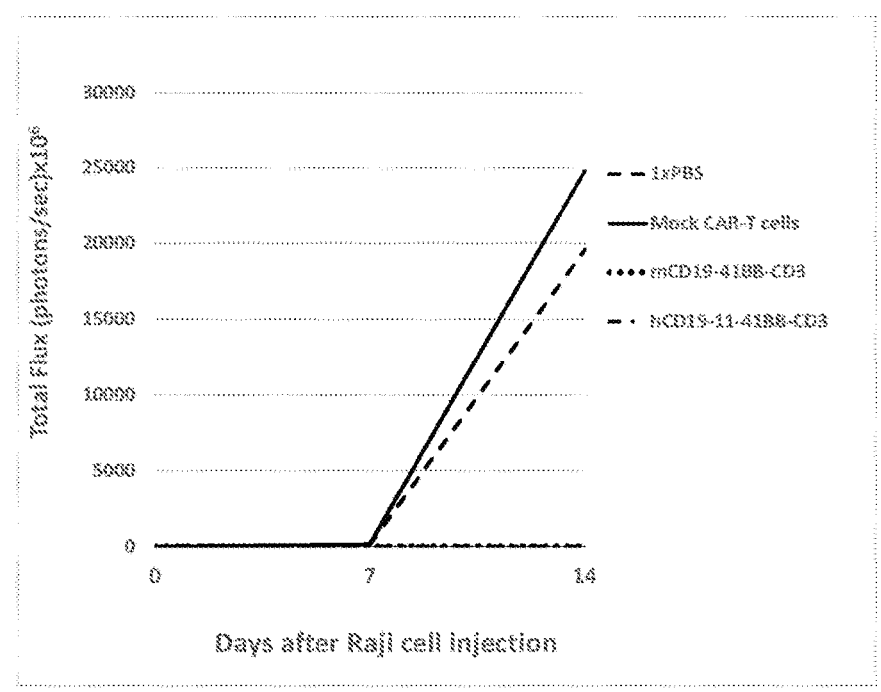
FIG. 8. Humanized CD19-CAR-T cells significantly decreased total flux (imaging signal) of Raji-luciferase xenograft tumors in NSG mice model in vivo. p<0.05 CD19-CAR-T cells vs Mock, 1×PBS treated mice.

The quantification of imaging at day 14 is shown in FIG. 8, which shows that both mouse and humanized CD19-CAR-T cells significantly decrease the imaging signal-total flux in photons/sec.

Figure 9:
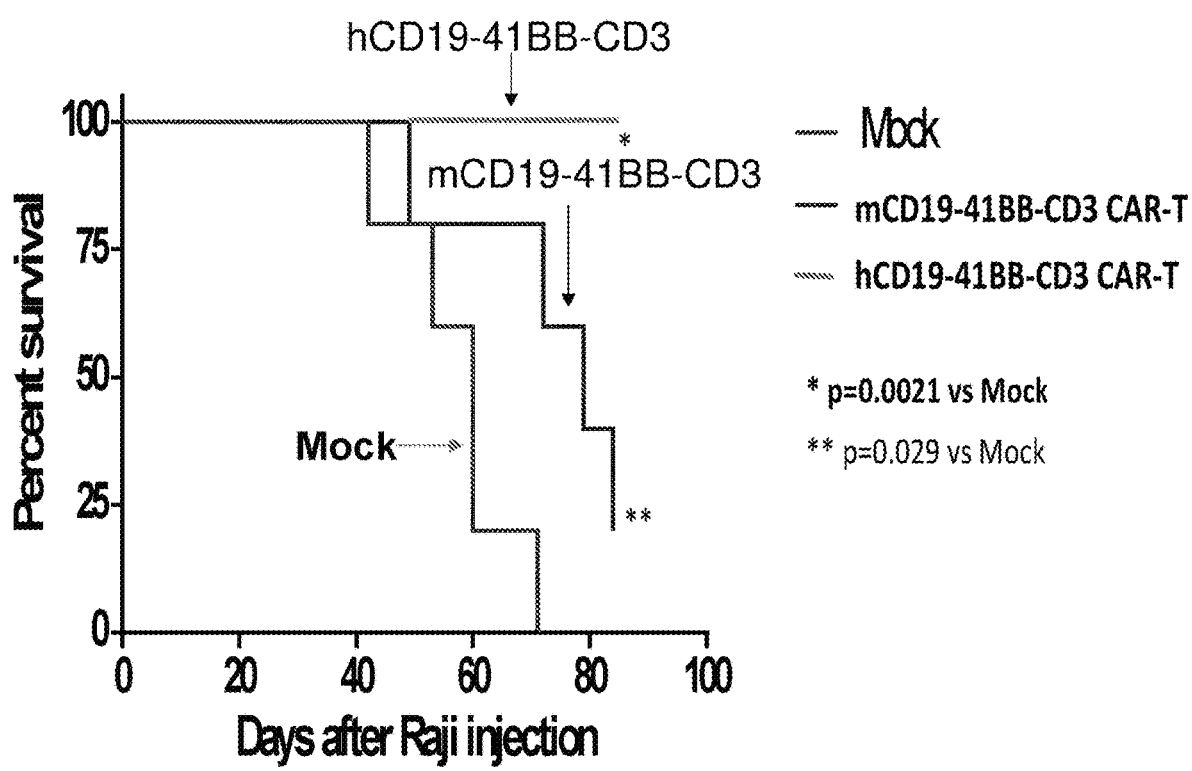
FIG. 9. Humanized CD19-CAR-T cells significantly prolonged survival of mice in Raji xenograft model. Kaplan-Meier survival curve shows that humanized CD19-CAR-T cells with mutation (V27G) in CDR1 region of VH significantly prolonged survival of mice versus mouse CD19-CAR-T cells and mock CAR-T cells. CAR-T cells were injected by i.v 1×10^7 cells/mice. *p<0.05, hCD19-41Bb-CD3 CAR-T cells vs Mock CAR-T cells; **p<0.05 mCD19-41BB-CD3 CAR-T cells vs Mock-CAR-T cells.

Example 7. Humanized CD19-CAR-T Cells Significantly Prolonged Survival of Mice in Raji Xenograft Model Over Mice Treated with Mouse CD19-CAR-T Cells The Kaplan-Meier survival curve shows a significant increase of survival in mice after injecting mice with humanized CD19-CAR-T cells versus mouse CD19-CAR-T cell or control Mock-Car-T cells (FIG. 9). This demonstrates advantage and increased efficacy of humanized CD19-CAR-T cells compared with mouse CD19-CAR-T cells.

Figure 10:
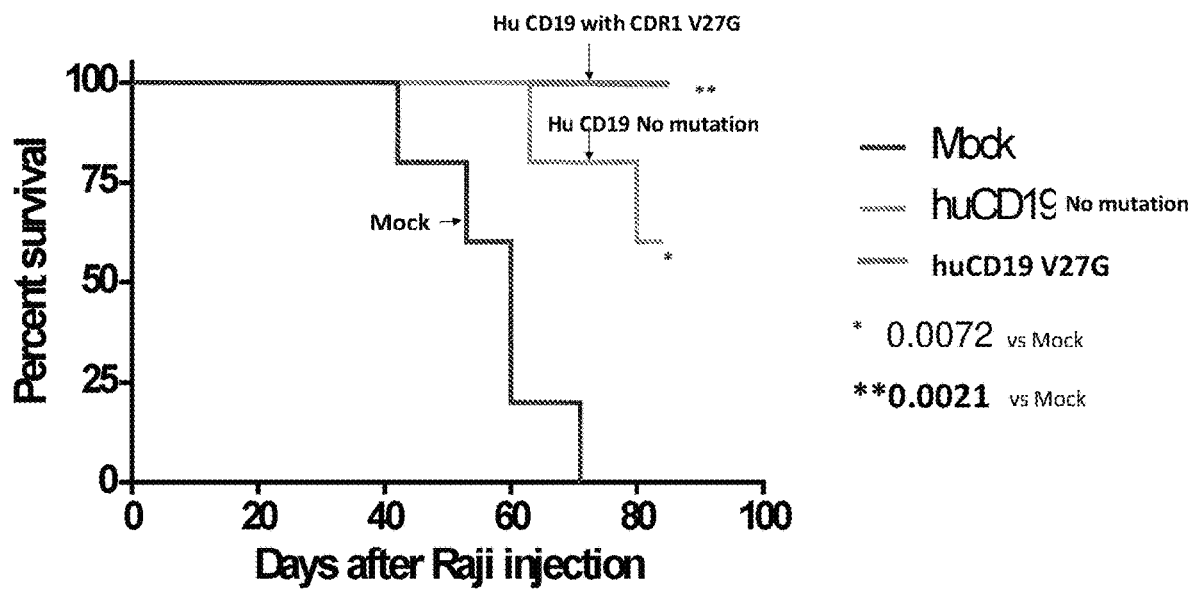
FIG. 10. Humanized CD19 CAR having mutation of V27G in CDR1 of VH prolonged survival of mice compared with mice treated with non-mutated humanized CD19 CAR-T cells.

Example 8. Humanized CD19 CAR with V27G in CDR1 of VH Prolonged Survival of Mice Compared with Mice Treated with Non-Mutated Humanized CD19 CAR-T Cells We compared humanized CD19-CAR with a V27G mutation in CDR1 of VH (Clone 11) with humanized CD19-CAR without a mutation. The "huCD19 no mutation" shown in FIG. 10 is a humanized antibody from mouse clone FMC63 without a mutation in CDR regions. The "huCD19 no mutation" and Clone 11 have the same VL sequence, but different frame region of VH. In general, antigen binding activity is affected by CDR regions, and not by framework regions.

The results in FIG. 10 show prolonged survival in mice treated with humanized CD19-CAR having a V27G mutation in VH than mice treated with humanized CD19-CAR-T cells without a mutation.

Example 9. CD19-CAR-T Cells are Detected by FACS with CD19 or FAB Antibody after Injection into Mice In Vivo The mouse blood was collected at day 7 after injecting CAR-T cells to mice with Raji xenograft tumor cells to detect CAR-T cells in vivo.

Figure 11:
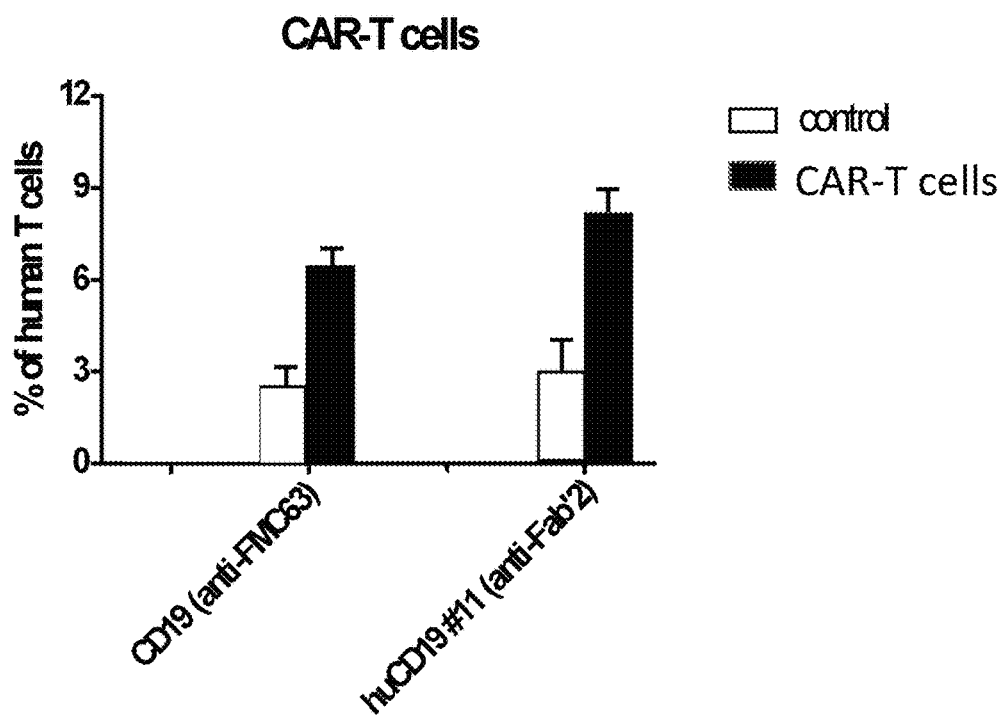
FIG. 11. Humanized CD19-CAR-T cells were detected by human FAB after injection into mice in vivo. Anti-FMC63 rabbit antibody detected mouse CD19-CAR-T cells; human anti-(Fab'2) antibody detected humanized CD19-CAR-T cells.

The result was shown in FIG. 11. CD19-CAR-T cells were readily detected after 7 days in mice in vivo with either Rabbit anti-FMC63 scFv antibody (Promab) for mouse CD19-CAR-T cells or with human FAB for humanized CD19-CAR-T cells. This suggests persistence of CAR-T cells in vivo that is consistent with significantly decreased Raji xenograft tumor growth.

REFERENCES

1. Maus, M. V.; Haas, A. R.; Beatty, G. L.; Albelda, S. M.; Levine, B. L.; Liu, X.; Zhao, Y.; Kalos, M.; June, C. H. T cells expressing chimeric antigen receptors can cause anaphylaxis in humans. *Cancer Immunol Res* 2013, 1, 26-31.
2. Maus, M. V.; Grupp, S. A.; Porter, D. L.; June, C. H. Antibody-modified t cells: Cars take the front seat for hematologic malignancies. *Blood* 2014, 123, 2625-2635.
3. Eshhar, Z.; Waks, T.; Gross, G. The emergence of t-bodies/car t cells. *Cancer J* 2014, 20, 123-126.
4. Berahovich, R.; Xu, S.; Zhou, H.; Harto, H.; Xu, Q.; Garcia, A.; Liu, F.; Golubovskaya, V. M.; Wu, L. Flag-tagged cd19-specific car-t cells eliminate cd19-bearing solid tumor cells in vitro and in vivo. *Front Biosci (Landmark Ed)* 2017, 22, 1644-1654.
5. Golubovskaya, V.; Berahovich, R.; Zhou, H.; Xu, S.; Harto, H.; Li, L.; Chao, C. C.; Mao, M. M.; Wu, L. Cd47-car-t cells effectively kill target cancer cells and block pancreatic tumor growth. *Cancers (Basel)* 2017, 9.

What is claimed is:

1. A humanized single-chain variable fragment (scFv) of CD19 comprising VH having the amino acid sequence of SEQ ID NO: 6 and VL having the amino acid sequence of SEQ ID NO: 5.

2. The scFv of claim 1, further comprises a linker in between VH and VL.

3. The scFv of claim 2, which has the amino acid sequence of SEQ ID NO: 4.

4. A chimeric antigen receptor (CAR) fusion protein comprising from N-terminus to C-terminus:
   (i) the scFv of claim 1,
   (ii) a transmembrane domain,
   (iii) at least one co-stimulatory domain, and
   (iv) an activating domain;
   wherein the CAR has the amino acid sequence of SEQ ID NO: 14.

5. An antibody against human CD19 comprising VH having the amino acid sequence of SEQ ID NO: 6 and VL having the amino acid sequence of SEQ ID NO: 5.

6. A nucleic acid molecule encoding the CAR fusion protein of claim 4.

7. A vector comprising the nucleic acid molecule of claim 6.

8. A host cell expressing the CAR fusion protein of claim 4.

9. A formulation comprising the cell of claim 8, and a pharmaceutically acceptable carrier, diluent or excipient.

10. The cell of claim 8, wherein the cell is T cell or NK cell.

11. A method for treating cancer or tumor comprising administering the cell of claim 8 to a subject in need of treatment.

* * * * *